United States Patent
Wack

(10) Patent No.: US 6,770,775 B2
(45) Date of Patent: Aug. 3, 2004

(54) METHOD OF SYNTHESIZING OPTICALLY ENRICHED α-HALO-ESTERS, AND PRODUCT AND COMPOSITION THEREFROM

(76) Inventor: Harald Wack, Tannenweg 27, Stammham (DE), 85134

( * ) Notice: Subject to any disclaimer, the term of this patent is extended or adjusted under 35 U.S.C. 154(b) by 120 days.

(21) Appl. No.: 09/861,221

(22) Filed: May 18, 2001

(65) Prior Publication Data

US 2003/0050501 A1 Mar. 13, 2003

(51) Int. Cl.[7] .................... C07C 69/76; C07C 69/62
(52) U.S. Cl. .................. 560/62; 560/100; 560/106; 560/145
(58) Field of Search .............. 560/145, 62, 100, 560/106

(56) References Cited

U.S. PATENT DOCUMENTS 4,728,458 A * 3/1988 Higuchi et al.
5,021,454 A * 6/1991 Sharma

FOREIGN PATENT DOCUMENTS

FR 2701706 A1 * 8/1994
GB WO 00/29505 A1 * 5/2000

OTHER PUBLICATIONS

Wack et al Journal of the American Chemical Society 2001, 123, pp. 1531–1532. + Supporting Information.*
Oppolzer et al Tetrahedron Letters 1985, 26(41), pp. 5037–5040.*
Hafez et al Organic Letters 2001, 3(13) pp. 3963–3965. Abstract Only.*

* cited by examiner

Primary Examiner—Michael L. Shippen
Assistant Examiner—Paul A. Zucker
(74) Attorney, Agent, or Firm—Stevens, Davis, Miller & Mosher, LLP

(57) ABSTRACT

A method of synthesizing highly optically enriched α-halo-esters comprises reacting acid halides with a cinchona alkaloid catalyst and a base to form intermediate ketenes. The ketenes are reacted with electrophilic halogenating reagents to produce α-halo-esters with high enantiomeric excess. The base can be an inorganic salt. The thus-formed α-halo-esters have utility in synthesizing other optically-pure materials.

13 Claims, 2 Drawing Sheets

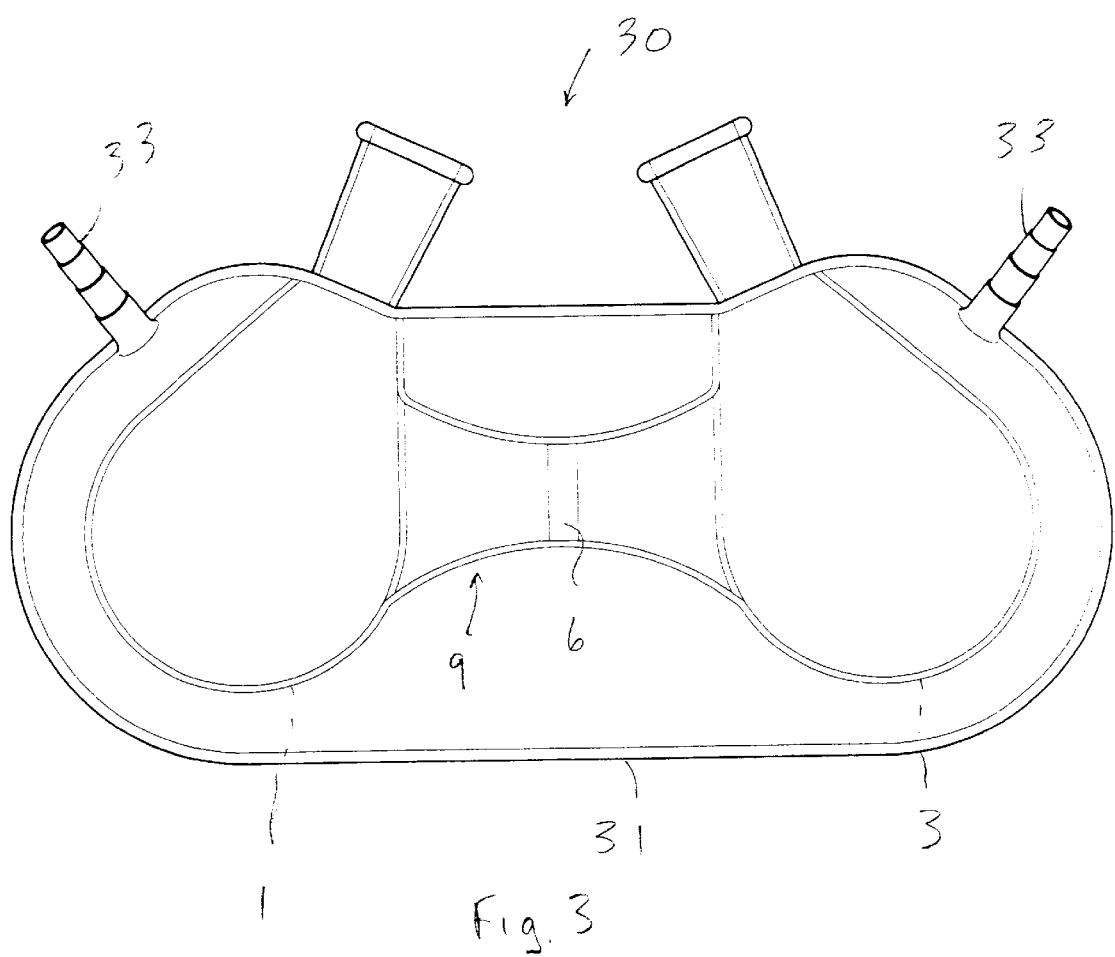

METHOD OF SYNTHESIZING OPTICALLY ENRICHED α-HALO-ESTERS, AND PRODUCT AND COMPOSITION THEREFROM

The present invention is directed to the synthesis of highly optically enriched α-halo-esters, and, in particular, to a synthesis method using acid halides, cinchona alkaloid catalysts and substituted halogenated quinones to produce α-halo-ketoesters.

BACKGROUND OF THE INVENTION

In the prior art, much effort is being expended into developing optically pure products as building blocks for the synthesis of various chemical, pharmaceutical, and agricultural products. These enantiomerically pure products exhibit high enantiomeric excess and are highly prized for their ability to serve as useful precursors for making optically active compounds such as amines, amides, ethers, and sulfides. Consequently, there is a need for improved methods for making these types of products, particularly halogen-containing products.

In the past, α-halogenation reactions have not been catalyzed due to the use of diatomic halides as halogenation reagents. These reagents can be highly reactive and in some cases very non-selective. However, since halocarbon products are desirable as intermediates, a need exists to produce chiral, optically active α-carbonyl halides for precursor use.

The present invention responds to this need by providing an asymmetric halogenation process to produce α-halo-esters. The process employs simple but effective catalyst and halogenation reagents, while producing an α-halo-ester having high enantiomeric excess.

SUMMARY OF THE INVENTION

It is a first object of the present invention to provide a method of making highly optically enriched α-halo-esters.

Another object of the invention is the product of the method of making the α-halo-esters.

Still another object of the invention is a method, which uses a double-sided flask in conjunction with the reaction sequences.

One other object of the invention is a composition comprising α-halo-esters having high enantiomeric excess, especially α-halo-ketoesters.

Other objects and advantages of the present invention will become apparent as a description thereof proceeds.

In satisfaction of the foregoing objects and advantages, the present invention provides a method of synthesizing an α-halo-ester by first reacting a solution containing a cinchona alkaloid catalyst, a base, and an acid chloride at low temperatures to produce an intermediate ketene solution. Then, a substituted halogenated quinone derivative is reacted with the ketene solution in the presence of the catalyst to produce the α-halo-ester having high enantiomeric excess. The catalyst is preferably one of benzoylquinine or benzoylquinidine, or their respective pseudoenantiomers, benzoylcinchonine or benzoylcinchonidine. The base can be a proton sponge, an inorganic salt, or a triaminophosphoamide immine. The inorganic salts can include potassium carbonate, potassium hydride, sodium carbonate, and sodium hydride and combinations thereof, or other first or second row carbonates.

In one mode, the intermediate ketene solution is filtered prior to conducting the halogenating reaction. The reaction and filtering can be done using a double-sided flask having two flasks separated by a filter. The ketene solution can be formed in one flask and then canted to the other flask through the filter for halogenation. The filter can be any type but is preferably a fritted disc filter disposed in a glass-tube connecting the two flasks.

The reaction to form the ketenes is controlled at a low temperature, preferably no higher than about −42° C. Low temperatures can be attained by cooling baths such as dry ice/acetone mixtures (−78° C.) or other equivalent means. Preferably, the reaction is conducted in a double-sided flask that is surrounded by another enclosing flask for precise control of temperature and atmosphere.

The invention also provides a new and novel highly optically pure/enriched composition and a product made from the inventive process. The (α-halo-ester composition has high enantiomeric excess, e.g., up to 99%, making it an ideal building block in other synthesis processes, wherein other optically pure products such as amides, sulfides, etc. can be made.

The inventive method also provides a unique halogenation synthesis process wherein the inorganic salts are used as a base. This mode offers significant advantages in terms of economics since the base materials are much less expensive than other base materials such as resins or the like.

BRIEF DESCRIPTION OF THE DRAWINGS

Reference is now made to the drawings of the invention wherein:

FIG. 3 shows an alternative flask including a surrounding chamber for reaction condition control.

DESCRIPTION OF THE PREFERRED EMBODIMENTS

Figure 1:
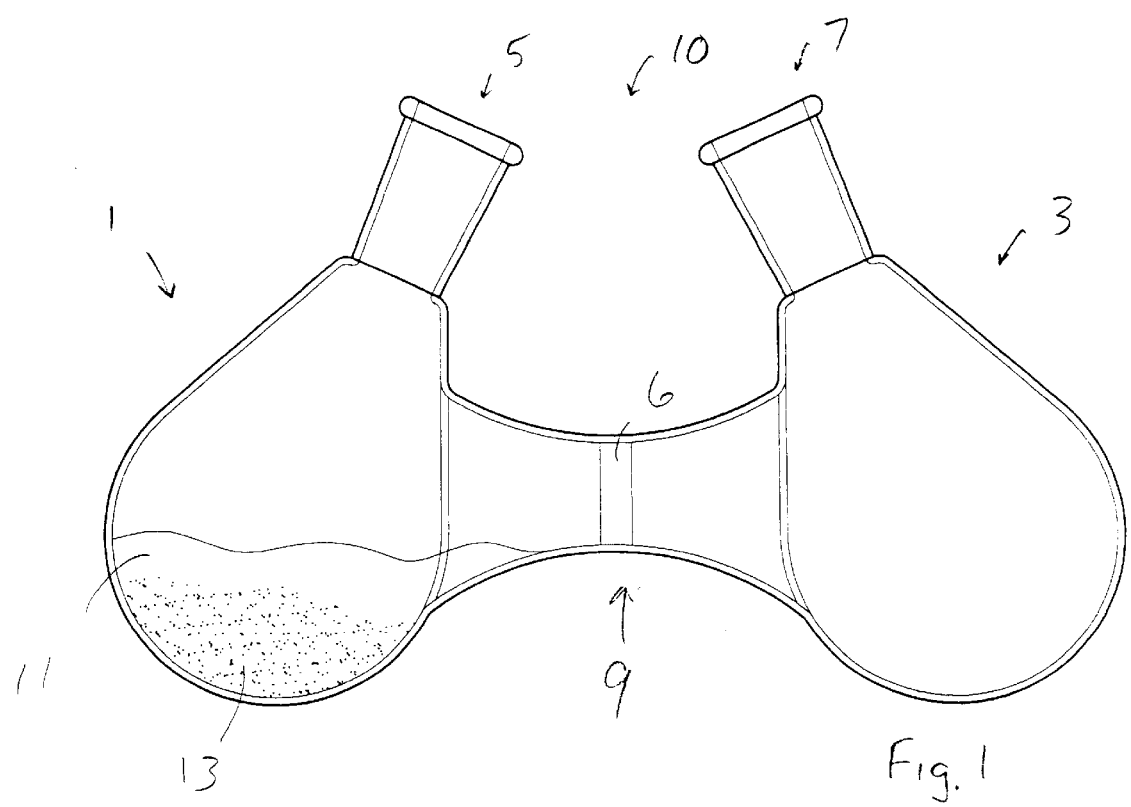
FIG. 1 is a side view of one example of a flask for use in a first stage of the inventive method.

The present invention offers significant advantages in the field of asymmetric catalytic halogenation reactions. Advantages include the making of products that are novel and have much utility in various applications, e.g., as building blocks in organic chemistry. The inventive α-halo-esters are of particular interest to the pharmaceutical industry due to the exhibition of two reactive centers. The products of the invention are the first commercially available chiral halogenated molecules.

The inventive method provides simplicity in that reagents of the reaction, acid halides and the substituted halogenated quinone systems, e.g. substituted di- or perhaloquinones, are both easily prepared. Further, virtually any acid halide can be used in the halogenating reaction.

Unlike most commercially available halogenated compounds that are racemic, i.e., % ee's that would be 0, the inventive method produces highly optically enriched α-halo-esters that exhibit high enantiomeric excess. Using prior art techniques, such halogenated compounds are not available.

The method also produces good yields in combination with the very high enantioselectivity, and such results are unprecedented for chlorinated, brominated, fluorinated or iodinated products, and believed applicable to fluorine and iodine halogens as well.

The use of inorganic salts in the reaction makes the process very economical as well.

The inventor's publications, i.e., Column Asymmetric Catalysis for β-Lactam Synthesis, *Organic Letters*, Vol. 2, number 25, pages 3963–3965, September, 2000, and Catalytic Asymmetric α-Halogenation, *J. Am. Cliem. Soc.* 2001, 123, 1531–1532, January, 2001, including its Supporting Information are hereby incorporated in their entirety by reference to the extent that they describe background information pertaining to this art.

The inventive method comprises a reaction between a number of reagents under controlled low temperature conditions. Broadly, the reaction can be characterized as the synthesis of highly optically enriched α-halo-esters from: (1) acid halides; (2) substituted halogenated quinone systems as an electrophilic halogenating agent; (3) cinchona alkaloid derivates as the catalyst; and (4) a base for the in-situ generation of ketenes as intermediate reaction products. The ketenes are primarily mono- or di-substituted ketenes and are produced via dehydrohalogenation (-HX) at the low temperatures.

In one mode, a triaminophosphoamide immine (BEMP resin) is used as a base in the production of the intermediate ketenes. In this mode, a jacketed addition funnel comprising a pair of columns can be used to first generate the ketenes, and then the final product, each under controlled conditions. More specifically, a jacketed additional funnel (2 cm wide) was plugged with a minimal amount of glass wool above its stopcock, and loaded under nitrogen with the BEGM resin (75 mg, 0.150 mmol) and an appropriately sized magnetic stir bar. It was then connected to a 10 ml three-neck round bottom flask that contained (0.015 mmol) catalyst 2a, benzoylquinine. Into the addition funnel 2 mL of THF was added and catalyst 2a was in turn dissolved in 1 ml of THF. The funnel and flask were cooled to −78° C. with a dry ice/acetone mixture. An overhead stirrer attached to a magnet was then positioned close to the jacketed funnel so that vigorous agitation of the heterogeneous BEMP/acid chloride solution was ensured. A solution of phenylacetyl chloride 1a (0.150 mmol) in THF (1 ml) was added dropwise into the funnel and vigorously stirred for 4 min. The stopcock was then opened to allow the ketene solution to drip by gravity into the bottom flask. The halogenating agent 5a (see Example 4) (0.150 mmol in 1 ml THF) was then added via syringe into the bottom flask. The reaction was kept at −78° C. for 3 h and then allowed to warm to room temperature. Absorption onto silica gel followed by column chromatography with hexanes as eluent afforded the S enantiomer 2-Chloro-2-phenyl-acetic acid pentachlorophenyl ester 80% yield and 99% ee.

Alternatively, and in a more preferred embodiment, the base is one of NaH, $K_2CO_3$, KH, CaH or $NaCO_3$, or combinations thereof, or other first or second row carbonates. When using one or more of the inorganic bases, the solids present as part of the first reaction step of ketene generation should be separated from the ketene solution as described below using the disclosed double-sided flask or an equivalent separating device. The double-sided flask can also be used when using the BEMP resin for the reaction sequence, if desired. When using the carbonates, there are no byproducts in the reaction since it produces bicarbonate and NaCl which are both solids, thus the need for filtering.

The catalyst is a chiral nucleophilic catalyst that activates the ketenes at low temperatures. A preferred catalyst is a benzoyl-protected quinine/quinidine, i.e., benzoylquinine or benzoylquinidine, or their respective pseudoenantiomers, benzoylcinchonine or benzoylcinchonidine, since this catalyst has two stereocenters, hence four diastereomer. While benzoylquinine produces the (S)-enantiomer, benzoylquinidine produces the (R)-enantiomer. Thus, you can make both enantiomers, depending on the catalyst you choose. These catalysts are chiral in nature, and inexpensive, thereby enhancing the economics of the reaction method. This presents an advantage over other synthesis processes employing expensive chiral catalysts.

While any acid halides can be used in the synthesis, exemplary halides include acid chlorides such as phenylacetyl chloride, 1-or 2-naphthylacetyl chloride, butyryl chloride, 3-phenoxypropionyl chloride, 4-methoxyphenyacetyl chloride, and acid bromides such as 2-bromoacetylbromide.

As stated above, the halogenating agent is an electrophilic perhaloquinone-derived reagent in which the "positive" halogen is transferred to the reactive intermediate ketene. Preferred examples include chlorinating agents such as 2,2,3,4,5,6-hexachlocyclohexdienone, and brominating agents such as 2,4,4,6-tetrabromo-2,5-cyclohexadienone. Examples of fluorinating and iodinating agents include 2,2,3,4,5,6 hexafluorocyclohexadienone and 4,4bromo, iodo, 2,3,5,6 tetrafluorocyclohexadienone.

The reaction begins with the combining of the base, catalyst and acid chlorides to generate the intermediate ketenes. This step is performed at low temperature to avoid problems with the ketene solution prior to the halogenating step. Once the reaction starts at the low temperature, the reactants are allowed to reach room temperature. The ketenes are primarily monosubstituted ketenes that are very reactive intermediates. Therefore, these reactions can only be performed at low temperature and under inert gas conditions (from a practical standpoint dry ice/acetone provides a desirable cooling bath having a temperature of −78° C.). Monosubstituted or di-substituted ketenes are very reactive and tend to dimerize at elevated temperatures (react with themselves), which renders them inactive and are thereby lost as the reaction partner. Thus, it is important to control the temperature of the reaction when generating the ketenes. While −78° C. is an exemplary temperature since a dry ice/acetone bath generally produces this temperature, the maximum temperature for the reaction should not exceed about −42° C. However, it should be understood that the low temperature is a starting temperature and that the reactants are then allowed to warm to room temperature over time., Thus, the reaction is believed to take place during the rising temperature, and that an absolute single temperature control is not deemed necessary to obtain the inventive products. It is believed that the reaction proceeds somewhere between the −78° C. starting temperature and 0° C.

As part of generating the intermediate ketene product, a solvent such as toluene or tetrahydrafuran can be employed to form solutions for the reactions. Other solvents can be employed as would be within the skill of the artisan in this regard.

Once the intermediate ketenes are generated, the halogenating agent is then added to the ketenes in the presence of the catalyst to produce the α-halo-ketoester having the high enantiomeric excess. As described below and in certain instances, e.g., when using the inorganic salts as base, a filtering step is performed prior to the addition of the halogenating agent.

Once the halogenating agent is added to the intermediate ketene solution under the low temperature conditions, the mixture can be brought to room temperature and the (α-halo-ketoester can be recovered using conventional techniques.

The reaction can be characterized as follows:

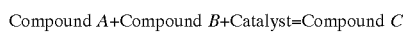

Compound A is the acid halide, and Compound B is the electrophilic halogenating agent. Compound C is the final α-halo-esters having the high enantiomeric excess or high % ee.

Prior to formation of Compound C, the reactive intermediate ketenes are formed from the acid halides or Compound A in the presence of the catalyst and the base, the base being either a proton sponge, a BEMP resin (a phosphazine base on a solid support thus allowing the resin to be treated as a solid), or an inorganic salt, see the examples below. These reactive intermediates then react with the halogenating reagent in the presence of the catalyst to form the α-halo-esters. As noted above, the temperature of the reactants must be low enough that the intermediate ketenes do not react with themselves and prevent the subsequent halogenation reaction to occur. Thus, the starting temperature of the reaction is controlled to be no higher than −42° C.

The reactions are also carried out in anhydrous air-free conditions. As can be seen from examples 6–11, the amounts of the acid chloride, the catalyst and the chlorinating or brominating agent are controlled based on molar equivalents. In these examples, the acid halide equivalent was 1.0, the catalyst was 0.1, and the halogenating agent was 1.0. An excess amount of the base inorganic salt was employed. The relative amounts can vary from those disclosed depending the reactants without departing from the scope of the invention. In example 1, the molar equivalent is 1.0 for both the acid halide and the halogenating agent.

The catalyst can be regenerated as disclosed in the inventor's Organic Letters publication, when using the BEMP resin as would be known in the art.

As noted above, in one mode of the invention, a base such as potassium carbonate ($K_2CO_3$) and/or sodium hydride (NaH) is used as part of the reaction in connection with the dehydrohalogenation step. Use of this base offers significant advantages in that the need for an expensive material such as the BEMP resin is avoided, thereby improving the economics of the process. While NaH and $K_2CO_3$ are exemplified in the examples discussed below, other bases such as $Na_2CO_3$ and KH are also believed to work as well in the reaction.

When using these bases, it is preferred to use a double-sided flask as shown in FIG. 1. This type of a flask allows for the separation of the solid material present as part of the dehydrohalogenation step of the reaction.

The double-sided flask is designated by the reference numeral 10 and includes two round-bottom flasks 1 and 3 connected (glass blown) to each other through their lower bodies via connection glass tube 5. Each flask 1 and 3 has an opening 5 and 7 respectively, to allow for the introduction of reagents as part of the inventive method. The connection glass tube 9 is equipped with a fritted disc 6 for separation.

The size of the flasks, their ground glass joint and specifics of the disc can vary depending on the desired application.

The glass connection tube can possibly be equipped with two male ground glass joints also. This necessitates that the two round bottom flasks are equipped with two female ground glass adapters. This option enables the user to easily disassemble the equipment.

Reactions can also be performed under various atmospheres, e.g. inert gas or other gases or atmospheres.

This double-sided flask also allows vacuum filtration. Other connections (e.g. valves, adapters) to the body or neck of each flask can also be employed. The flasks can also be surrounded by another enclosure, which would permit maintaining the flasks under certain conditions. For example, the reaction can be kept under low temperatures, by filling the surrounding enclosure with a dry ice/acetone or other media, which would maintain the reagents at the desired low temperature for reaction purposes. The enclosure can be equipped with the necessary connections and the like to facilitate the temperature control over the flasks as needed to ensure that the reaction is held at the proper temperature for the proper time period. FIG. 3 shows an exemplary double-sided flask 30 with an enclosure 31, the enclosure having inlets/outlets 33.

Figure 2:
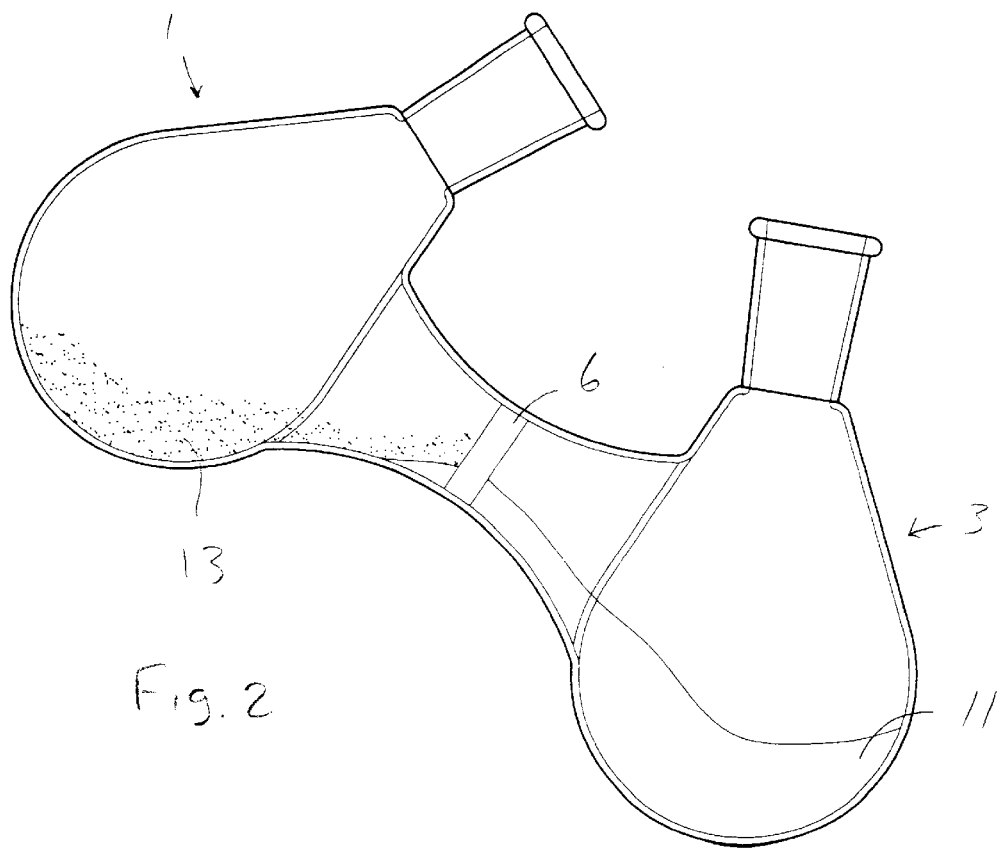
FIG. 2 shows the flask infuse in a separation step of the inventive method.

FIG. 1 shows the reaction stage wherein the ketene solution 11 and solids 13 are produced in flask 1 as part of the dehydrohalogenation step. By tipping flask 3 as shown in FIG. 2, the ketene solution 11 passes through the filter or fritted glass disc 6 into flask 3, with the solid material 13 remaining in flask 1. The double-sided flask allows this step to be done under controlled low temperature conditions so as not to adversely affect the ketene,solution. Once the ketene solution is in flask 3, the halogenation reaction can proceed with the halogenating agents. When using a fritted disc, different pore sizes can be selected, the finer the fritt, the slower the filtering rate. With bigger frits, fine salts such as hydrides can pass through so it is important to select the right filter for the particular solids being filtered.

When using the double-sided flask, flask 1 can be charged with the inorganic salt and catalyst with the other half being charged with the catalyst. A solvent such as toluene is employed to form a solution and can be added to each flask side.

The acid halide is then added to flask 1 and the mixture is stirred for a predetermined period of time, e.g., 12 hours under the low temperature conditions created by a dry ice/acetone bath surrounding flask 1, see FIG. 3. This generates the ketenes and solids in flask 1. The flask 1 is then canted so that the ketenes pass through the filter 6 and into flask 3 containing the catalyst solution. The (α-halo-ketoester forms in flask 3 and is recovered using conventional techniques. It should be noted that this technique is much simpler than the technique described in the inventor's *Organic Letters* wherein a jacketed dual column assembly was employed, the upper column producing the ketenes and the lower column producing the halogenated product.

The primary uses of the double-sided flask include filtering heterogeneous (e.g. solid/liquid) mixtures, the generation of low temperature reaction intermediates, performing two independent reactions in each flask, and combining two reaction vessels into one.

The double-sided flask is advantageous by allowing any reaction that involves a filtration step can now be performed in one reaction vessel.

Further, by employing the double-sided flask, reaction intermediates that are unstable at higher temperatures can be kept at desired conditions (e.g. −78° C.). Prior art filtration equipment always involved parts, which could not be fully temperature-regulated.

Using the double-sided flask, filtration is easily performed through slightly tilting the apparatus to one side.

Because the system can be immersed in or surrounded by a cooling bath, vacuum filtration will not evaporate any solvent. Therefore, the concentration of the solution can be kept constant.

The double-sided flask allows for two independent reactions to be combined at any time.

A number of studies were conducted in connection with the inventive method, and the details are set forth below. It should be understood that the various reagents and procedures are exemplary and are not to be considered as limiting the scope of the invention.

As part of the experimental studies, eleven examples are listed with each; example defining the reagents, amounts of reagents, experimental procedures and results.

Example 1 shows the reaction using a proton sponge with Example 2 using a bromoketene with a 1.2 equivalents of catalyst, the catalyst acting as a base (1.0 equiv) and as a catalyst (0.2 equiv). Example 3 shows the procedure to prepare the halogenating agent. Examples 4 and 5 use a jacketed funnel, with Example 5 using the BEMP resin. The jacketed addition funnel arrangement is described in the Organic Letters publication incorporated by reference.

Examples 6–11 differ from the previous examples by using a brominating agent as the electrophilic halogenating agent, and potassium carbonate as the base material. In certain of these examples, a little more ketene was used than halogenating agent to anticipate ketene dimerization. As is evident from the results of these examples, the final α-haloketoesters have high enantiomeric excess values as well as yields in excess of 50%.

EXAMPLE 1

Reagents

Phenylacetylchloride (compound A): Molecular Mass (MM): 155 g/mol; mass used (m): 100 mg; Mol (n)=6.45× $10^{-4}$ mol; equivalents (equiv.): 1

Proton sponge: MM: 206.3; m=140 mg; n=6.7×$10^{-4}$ mol; equiv.=1.05 2,2,3,4,5,6-Hexachlorocyclochexdienone (compound 5a): MM: 300.8; m=194 mg; n=6.45×$10^{-4}$ mol; equiv.=1

Benzoylquinine (catalyst): MM=424; m=27 mg; n=6.45×$10^{-5}$ mol; equiv.=10%

Procedure

Proton Sponge and benzoylquinine were dissolved in 2.5 ml tetrahydrofuran (THF), freshly distilled. This solution was then cooled to −78° C. before the phenylacetylchloride was added as a 1 ml solution in THF. It was allowed to stir for 5 minutes, before compound B (2,2,3,4,5,6-Hexachlorocyclochexdienone) was added also as a 1 ml solution in THF. After addition was complete, the color changed to bright red. The solution was allowed to warm up overnight to give a red solution with precipitation.

Results

Reaction was absorbed onto silica gel and column-chromatographed (CC) with straight hexane to give the desired product in 30% yield.

EXAMPLE 2

Reagents

2-Bromoacetylbromide: (compound A): Molecular Mass (MM): 201.85 g/mol; mass used (m): 100 mg; Mol (n)=4.954×$10^{-4}$ mol; equivalents (equiv.): 1

2,2,3,4,5,6-Hexachlorocyclochexdienone (compound B): MM: 300.8; m=150 mg; n=6.45×$10^{-4}$ mol; equiv.=1

Benzoylquinine: MM=424; m=252 mg; n=5.94×$10^{-4}$ mol; equiv.=1.2 (1.0 as base and 0.2 as catalyst)

Procedure

Quinine was weighed out in the dry box. Toluene was freshly distilled from sodium (Na). Quinine was then dissolved in 15 ml of toluene and cooled with a dry ice/ether bath. After 10 minutes, the bromoacidbromide was added as a 1 ml solution in toluene (see below for details of preparing the cooling bath). After 10 minutes, the hexachlorocyclochexdienone was added also as a 1 ml solution in toluene.

Cooling bath details: The ether/ether bath only cooled to −80° C., and then liquid nitrogen was added to it and it froze. To this, mix EtOH was added and the clear cooling solution then reached −110° C.

The bromoacidbromide as a 1 ml solution in toluene was then added. At that point the solution turned yellow. To this, the hexachlorocyclochexdienone was added also as a 1.5 ml solution in toluene, and the solution was allowed to warm up overnight.

Results

Yield after CC: 90 mg or 50%. Ee:>95%.

Example 3 (halogenating compound making—known conventionally)

Pentachlorophenol was dissolved in 15 ml of freshly distilled carbon tetrachloride, but wasn't completely soluble. But upon addition (at room temperature) of tert-butylhypochlorite (prepared according to known procedures) it dissolved completely. Stirred for three hours at room temperature (RT).

Pumped on it overnight (High vacuum) to give a yellow solid residue.

Recrystallized from Petroleum Ether (PetEther). Filtered under Nitrogen and Infrared (IR) showed C=O bonds having characteristic bands at around 1715 $cm^{-1}$.

EXAMPLE 4

Phenylacetylchloride (compound 1a): Molecular Mass (MM): 155 g/mol; mass used (m): 100 mg; Mol (n)=6.45×$10^{-4}$ mol; equivalents (equiv.): 1

Benzoylquinine (compound 2a): MM=424; m=71 mg; n=1.29×$10^{-4}$ mol; equiv.=20%

NaH (Sodium hydride): MM=24; m=26 mg(60% dispersion in oil); n=6.45×$10^{-4}$ mol; equiv.=1.0

2,2,3,4,5,6-Hexachlorocyclochexdienone (compound 5a): MM: 300.8; m=190 mg; n=2.3×$10^{-4}$ mol; equiv.=0.75

In a 25 ml round bottom flask the benzoylquinine and NaH (60% dispersion in mineral oil) were weighed out. Phenylacetylchloride and hexachlorocyclochexdienone were each weighed out separately. 6 ml of THF were added to the 25 ml flask and the resulting white suspension cooled to −78° C.

Phenylacetylchloride was prepared as a 1 ml solution in THF and added to the flask. No visible reaction occurred, it was still a suspension.

1 drop of N,N-Dimethylformamide (DMF) was added to it, No change.

3 more drops were added and stirred for 2 hours. Warmed to −10 and then to 20° C. Nothing happened.

Added hexachlorocyclochexdienone as 1 ml solution in THF at −78° C. dropwise. Nothing happened, warmed up to room temperature. TLC (ThinLayerChromatography) indicated product formation.

EXAMPLE 5

Reagents

Phenylacetylchloride (compound A): Molecular Mass (MM): 155 g/mol; mass used (m):100 mg; Mol (n)=6.45×$10^{-4}$ mol; equivalents (equiv.): 1

Benzoylquinine (the catalyst): MM=424; m=27 mg; n=6.45×$10^{-5}$ mol; equiv.=10%

2,2,3,4,5,6-Hexachlorocyclochexdienone (compound 5a): MM: 300.8; m=45 mg; n=6.45×$10^{-4}$ mol; equiv.=1.0

BEMP, a triaminophosphoamide immine bound to a polymeric support: 2 mmol/g, n=7.1×$10^{-4}$ mol; equiv.=1.1

Procedure

The mix of BEMP, the acid chloride, and the catalyst were vigorously agitated for 4 minutes under low temperatures (−78° C.). The agitated mixture (the ketene solution) was then fed into the bottom of the flask and 1 ml solution of hexachlorocyclochexdienone in THF was added to it. (The specific procedure is explained in the Organic Letters publication.)

Results

Product after CC: 37 mg or 55%. Ee: 97%.

EXAMPLE 6

(this example and the following used twice as much ketene relative to the brominating agent, anticipating that the high reactivity of the monosubstituted ketenes might result in dimerization)

| Reagents | MW | mmol | mg | eq |
|---|---|---|---|---|
| Phenylacetyl Chloride | 155 | 0.13 | 20 | 1.0 |
| 2,4,4,6-Tetrabromo-2,5-cyclohexadien-1-one | 410 | 0.07 | 29 | 0.5 |
| Benzoylquinine | 427 | 0.013 | 6 | 0.1 |

Procedure

In the dual reaction/filtration flask
One side of flask was charged with excess potassium carbonate and 5 mol % benzoylquinine.
The other half was charged with just 5 mol % benzoylquinine.
3 ml of toluene was added to the carbonate side and 1 ml was added to the benzoylquinine side.
The flask was cooled to −78° C. in a dry ice/acetone bath.
The acid chloride was added to the carbonate and the reaction was stirred for 12 hours at −78° C.
The flask was then canted and the ketene solution is filtered to the other side of the flask
The brominating agent is added to the reaction
The reaction is allowed to warm to room temperature overnight Results Product formed: (S)-2-Bromo-2-phenylacetic acid (2,4,6-tribromophenyl) ester
75% yield
91% ee

EXAMPLE 7

| Reagents | MW | mmol | mg | eq |
|---|---|---|---|---|
| Phenoxylpropioyl Chloride | 184 | 0.13 | 24 | 1.0 |
| 2,4,4,6-Tetrabromo-2,5-cyclohexadien-1-one | 410 | 0.07 | 29 | 0.5 |
| Benzoylquinine | 427 | 0.013 | 6 | 0.1 |

Procedure

In the dual reaction/filtration flask
One side of flask was charged with excess potassium carbonate. and 5 mol % benzoylquinine.
The other half charged with 5 mol % benzoylquinine.
3 ml of toluene was added to the carbonate side and 1 ml was added to the benzoylquinine side.
The flask was cooled to −78° C. in a dry ice/acetone bath.
The acid chloride was added to the carbonate and the reaction was stirred for 12 hours at −78° C.
The flask is canted and the ketene solution is filtered to the other side of the flask
The brominating agent is added to the reaction
The reaction is allowed to warm to room temperature overnight Results Product formed: (S)-2-Bromo-3-phenoxypropionic acid (2,4,6-tribromophenyl) ester
68% yield
98% ee

EXAMPLE 8

| Reagents | MW | mmol | mg | eq |
|---|---|---|---|---|
| Butyryl Chloride | 106 | 0.13 | 14 | 1.0 |
| 2,4,4,6-Tetrabromo-2,5-cyclohexadien-1-one | 410 | 0.07 | 29 | 0.5 |
| Benzoylquinine | 427 | 0.013 | 6 | 0.1 |

Procedure

In the dual reaction/filtration flask
One side of flask was charged with excess potassium carbonate and 5 mol % benzoylquinine.
The other half charged with 5 mol % benzoylquinine.
3 ml of toluene was added to the carbonate side and 1 ml was added to the benzoylquinine side.
The flask was cooled to −78° C. in a dry ice/acetone bath.
The acid chloride was added to the carbonate and the reaction was stirred for 12 hours at −78° C.
The flask is canted and the ketene solution is filtered to the other side of the flask
The brominating agent is added to the reaction
The reaction is allowed to warm to room temperature overnight Results Product formed: (S)-2-Bromo-2-butyric acid (2,4,6-tribromophenyl) ester
58% yield
86% ee

EXAMPLE 9

| Reagents | MW | mmol | mg | eq |
|---|---|---|---|---|
| 2-Napthylacetyl Chloride | 204 | 0.13 | 27 | 1.0 |
| 2,4,4,6-Tetrabromo-2,5-cyclohexadien-1-one | 410 | 0.07 | 29 | 0.5 |
| Benzoylquinine | 427 | 0.013 | 6 | 0.1 |

Procedure

In the dual reaction/filtration flask
One side of flask was charged with excess potassium carbonate and 5 mol % benzoylquinine.
The other half charged with 5 mol % benzoylquinine.
3 ml of toluene was added to the carbonate side and 1 ml was added to the benzoylquinine side.
The flask was cooled to −78° C. in a dry ice/acetone bath.
The acid chloride was added to the carbonate and the reaction was stirred for 12 hours at −78° C.
The flask is canted and the ketene solution is filtered to the other side of the flask The brominating agent is added to the reaction The reaction is allowed to warm to room temperature overnight Results Product formed: (S)-2-Bromo-2-(2-napthyl)acetic acid (2,4,6-tribromophenyl) ester 68% yield 94% ee

EXAMPLE 10

| Reagents | MW | mmol | mg | eq |
|---|---|---|---|---|
| 1-Napthylacetyl Chloride | 204 | 0.13 | 27 | 1.0 |
| 2,4,4,6-Tetrabromo-2,5-cyclohexadien-1-one | 410 | 0.07 | 29 | 0.5 |
| Benzoylquinine | 427 | 0.013 | 6 | 0.1 |

Procedure

In the dual reaction/filtration flask

One side of flask was charged with excess potassium carbonate and 5 mol % benzoylquinine.

The other half charged with 5 mol % benzoylquinine.

3 ml of toluene was added to the carbonate side and 1 ml was added to the benzoylquinine side.

The flask was cooled to −78° C. in a dry ice/acetone bath.

The acid chloride was added; to the carbonate and the reaction was stirred for 12 hours at −78° C.

The flask is canted and the ketene solution is filtered to the other side of the flask The brominating agent is added to the reaction The reaction is allowed to warm to room temperature overnight Results Product formed: (S)-2-Bromo-2-(1-Napthyl)acetic acid (2,4,6-tribromophenyl) ester 71% yield 98% ee

EXAMPLE 11

| Reagents | MW | mmol | mg | eq |
|---|---|---|---|---|
| 4-Methoxyphenylacetyl Chloride | 185 | 0.13 | 24 | 1.0 |
| 2,4,4,6-Tetrabromo-2,5-cyclohexadien-1-one | 410 | 0.07 | 29 | 0.5 |
| Benzoylquinine | 427 | 0.013 | 6 | 0.1 |

Procedure

In the dual reaction/filtration flask

One side of flask was charged with excess potassium carbonate and 5 mol % benzoylquinine.

The other half charged with 5 mol % benzoylquinine.

3 ml of toluene was added to the carbonate side and 1 ml was added to the benzoylquinine side.

The flask was cooled to −78° C. in a dry ice/acetone bath.

The acid chloride was added to the carbonate and the reaction was stirred for 12 hours at, −78° C.

The flask is canted and the ketene solution is filtered to the other side of the flask The brominating agent is added to the reaction The reaction is allowed to warm to room temperature overnight Results Product formed: (S)-2-Bromo-2-(p-methoxyphenyl) acetic acid (2,4,6-tribromophenyl) ester 73% yield 89% ee The experimental studies listed above show that a high optically active α-halo-ketoester, i.e., one with high enantiomeric excess, can be synthesized using the inventive reaction. This highly enantiomeric product has great utility as branch points in the synthesis of numerous functionalized molecules.

For example, an α-halo-ester, (S)-2-chloro-2-phenyl-acetic acid pentachlorophenyl ester, was produced by the inventive reaction when using the BEMP resin as a base. This enantiomer, having a 90% ee with a yield of 80%, was mixed with one equivalent of benzylarnine at room temperature in tetrahydrofuran for two hours. The reaction was then quenched with $NaHCO_3$. The aqueous solution was extracted three times with 5 ml of $Et_2O$ and the combined organic extracts were dried with $Na_2SO_4$. Absorption onto silica gel followed by column chromatography with hexanes as eluent afforded an optically pure derivatized amide, (S)-N-benzyl-2 chloro-2-phenyacetamide having a 99% yield and 99% ee. The racemic form of this amide is known to exhibit powerful anticonvulsant activity. It should be understood that this application is just one example of the use of the inventive α-halo-esters and other uses are within the scope of the invention.

As such, an invention has been disclosed in terms of preferred embodiments thereof, which fulfills each and every one of the objects of the present invention as set forth above and provides new and improved method of making an α-halo-ketoester as well as α-halo-ketoester products.

Of course, various changes, modifications and alterations from the teachings of the present invention may be contemplated by those skilled in the art without departing from the intended spirit and scope thereof. It is intended that the present invention only be limited by the terms of the appended claims.

I claim:

1. A method of synthesizing an α-halo-ester comprising:
   a) reacting a solution containing a benzolyated cinchona alkaloid catalyst, a base, and an acid chloride at low temperatures to produce an intermediate ketene solution; and
   b) reacting a substituted halogenated quinone derivative with the ketene solution in the presence of the catalyst to produce the α-halo-ester having high enantiomeric excess.

2. The method of claim 1, wherein the catalyst is one of a benzoylquinine, benzoylquinidine, benzoylcinchonine or benzoylcinchonidine.

3. The method of claim 1, wherein the base is an inorganic salt.

4. The method of claim 1, wherein the base is a triaminophosphoamide imine.

5. The method of claim 1, wherein the intermediate ketene solution is filtered prior to step (b).

6. The method of claim 1, wherein a double-sided flask having two flasks separated by a filter is used for filtering, the ketene solution formed in one flask and then canted to the other flask through the filter for step (b).

7. The method of claim 3, wherein the inorganic salt is selected from the group consisting of first and second row carbonates, and hydrides, and combinations thereof.

8. The method of claim 1, wherein step (a) is initially conducted at a temperature no higher than −42° C., and then the temperature is increased to room temperature.

9. In a method of making an α-halo-ester wherein a solution of a benzoylated cinchona alkaloid catalyst, a base, and an acid chloride at low temperatures are reacted to produce an intermediate ketene solution; and a substituted halogenated quinone derivative is reacted with the intermediate ketene solution in the presence of the catalyst to produce the α-halo-ester having high enantiomeric excess, the improvement comprising using an inorganic salt as the base.

10. The method of claim 9, wherein the inorganic salt is selected from the group consisting of first and second row carbonates and hydrides and combinations thereof.

11. The method of claim 9, wherein the intermediate ketene solution is filtered prior to reaction with the substituted halogenated quinone derivative.

12. The method of claim 11, wherein a double-sided flask having two flasks separated by a filter is used for filtering, the ketene solution formed in one flask and then canted to the other flask through the filter for step (b).

13. The enantomeric α-halo-ester of claim 9, wherein the α-halo-ester is selected from the group consisting of:
1) (S)-2-Bromo-2-phenylacetic acid (2,4,6-tribromophenyl) ester;
2) (S)-2-Bromo-3-phenoxypropionic acid (2,4,6-tribromophenyl) ester;
3) (S)-2-Bromo-2-butyric acid (2,4,6-tribromophenyl) ester;
4) (S)-2-Bromo-2-(2-napthyl)acetic acid (2,4,6-tribromophenyl) ester;
5) (S)-2-Bromo-2-(1-napthyl)acetic acid (2,4,6-tribromophenyl) ester; and
6) (S)-2-Bromo-2-(p-methoxyphenyl)acetic acid (2,4,6-tribromophenyl) ester.

* * * * *